(12) United States Patent
Ide

(10) Patent No.: US 6,527,706 B2
(45) Date of Patent: Mar. 4, 2003

(54) INSERTION INSTRUMENT OF AN ENDOSCOPE

(75) Inventor: Masao Ide, Omiya (JP)

(73) Assignee: Fuji Photo Optical Co., Ltd., Omiya (JP)

(*) Notice: Subject to any disclaimer, the term of this patent is extended or adjusted under 35 U.S.C. 154(b) by 0 days.

(21) Appl. No.: 09/773,912

(22) Filed: Feb. 2, 2001

(65) Prior Publication Data
US 2001/0023313 A1 Sep. 20, 2001

(30) Foreign Application Priority Data
Feb. 3, 2000 (JP) .................................... 2000-026120

(51) Int. Cl.⁷ ............................................... A61B 1/00
(52) U.S. Cl. ........................ 600/142; 600/139; 600/146
(58) Field of Search ................................ 600/139, 140, 600/141, 142, 146, 149, 95.04

(56) References Cited

U.S. PATENT DOCUMENTS 4,773,395 A * 9/1988 Suzuki et al. ............... 138/120
5,591,120 A * 1/1997 Machida et al. ............ 138/120

FOREIGN PATENT DOCUMENTS

JP 411225948 A * 8/1999
JP 411235305 A * 8/1999

* cited by examiner

*Primary Examiner*—Linda C. M. Dvorak
*Assistant Examiner*—Kenneth G Schopfer
(74) *Attorney, Agent, or Firm*—Oblon, Spivak, McClelland, Maier & Neustadt, P.C.

(57) ABSTRACT

In an endoscopic insertion instrument having a rigid tip end section, an elongated flexible body, and an angle section connected between the rigid tip end section and the flexible body, a joint construction connects an angle section to the fore end of the flexible body. A couple of connecting rings are provided opposingly at joining ends of the angle section and the flexible body. At least one aperture is provided in an outer one of the connecting rings to feed a flux. At least one angle section operating is passed through the connecting ring. The operating wire is encased in a sheathing coil, the fore end of which is fixed to the inner one connecting rings. To prevent flux from getting into the closed sheathing coil, a shield portion is formed around an outer periphery of the sheating coil over a predetremined range in axial length.

10 Claims, 7 Drawing Sheets

INSERTION INSTRUMENT OF AN ENDOSCOPE

BACKGROUND OF THE INVENTION

1. Field of the Art

This invention relates to an endoscopic insertion instrument which is suitable for use in medical examinations, and more particularly to an endoscopic insertion instrument having a wire guide mechanism incorporated into a flexible body portion of the insertion instrument for guiding operating wires which are pulled back and forth at the time of flexibly bending an angle section of the instrument.

2. Prior Art

As for endoscopes of medical use, for example, it has been known to employ an insertion instrument of the construction as shown in FIG. 5. In that figure, indicated at 1 is a manipulating head, at 2 an elongated insertion instrument and at 3 a universal cable. A major part of the elongated insertion instrument 2 is constituted by a flexible body section 2a which is connected to the manipulating head 1 at its proximal end. An angle section 2b is connected to the fore end of the flexible body section 2a, and further a rigid tip end section 2c is connected to the fore end of the angle section 2b. Illumination means as well as image pickup means are mounted on or in the rigid tip end section 2c. The angle section 2b is flexibly bendable to turn the rigid tip end section 2c into desired directions. The flexible body section 2a is also arranged to be arbitrarily bendable along a path of insertion at the time of introduction into a body cavity.

Illustrated in FIG. 6 is a joint portion which connects the angle section 2b with the flexible body section 2a of the insertion instrument. Incorporated into the flexible body 2a, which is required to be bendable in arbitrary directions, is a flexible coil shaft 10 which is formed by helically winding narrow metal strips. Generally, the coil shaft 10 is of a double-coil tube construction consisting of two coil windings of opposite directions. The coil tube 10 is enshrouded in a mesh layer 11 which is in turn enshrouded in a flexible outer skin layer 12.

On the other hand, the angle section 2b is flexibly bent into an angular form by remote control from an angle knob 4 which is provided on the manipulating head 1 of the endoscopic insertion instrument. In construction, the angle section 2b is constituted by a series of angle rings 13 which are pivotally connected one after another by means of vertically and transversely aligned pivoting pins 14. Namely, preceding and succeeding angle rings 13 which are pivotally connected with each other by means of a pair of pivoting pins 14 are pivotally flexible relative to each other in a direction perpendicular to an axis of the paired pivoting pins 14. Further, the angle rings 13 are connected successively and alternately by vertically aligned pivoting pins and transversely aligned pivoting pins, so that the angle section 2b can be turned arbitrarily in upward and downward directions as well as rightward and leftward directions. Similarly to the elongated flexible body 2a, the angle rings 13 of the angle section 2b are wrapped in successively by a mesh layer 15 and a flexible outer skin layer 16.

As described above, the flexible body 2a and angle section 26 of the endoscopic insertion instrument distinctively differ from each other in construction. Therefore, it is after the flexible body 2a and the angle section 2b are assembled separately that a proximal end portion of the angle section 2b is connected to a fore end portion of the flexible body 2a of the insertion instrument. For the purpose of connecting the flexible body 2a and the angle section 2b with each other, connecting rings 17 and 18 are provided on the flexible body 2a and the angle section 2b, respectively. Namely, a connecting ring 17 is securely fixed, for example, by welding to the fore end of the coil tube 10 of the flexible body 2a. On the other hand or on the side of the angle section 2b, a connecting ring 18 which constitutes a rearmost angle ring of the angle section 2b is pivotally connected to an adjacent angle ring 13 by pivoting pins 14. Alternatively, the connecting ring 18 can be securely fixed to a rearmost angle ring by welding if desired.

The angle section 2b is connected to the flexible body 2a of the insertion instrument by partly fitting the connecting ring 18 into the connecting ring 17 on the side of the flexible body 2a. The connecting ring 17 on the side of the flexible body 2a, which is located on the outer side of the connecting ring 18, is provided with an aperture or apertures 19. Solder 20 is filled into the apertures 19 to fix the two connecting rings 17 and 18 to each other in a securely connected state. The outer skin layer 12 of the flexible body 2a is butted against the outer skin layer 16 of the angle section 2b. A line wrapping is formed across the butted ends of the outer skin layers 12 and 16, and an adhesive is applied on the line wrapping. Thus, the angle section 2b is connected to the flexible body 2a almost seamlessly.

In this instance, fitted in the insertion instrument 2 are various component parts, including a light guide consisting of a bundle of fiber optics for transmission of illumination light, a signal cable in the case of an electronic endoscope (an image guide consisting of a bundle of fiber optics in the case of an optical endoscope), a biopsy channel, an air/water feed channel etc. Operating wires are 21 also fitted in the insertion instrument 2 in order to flexibly bend the angle section 2b by remote control. A couple of operating wires are threaded in upper and lower positions in the insertion instrument 2 in case the angle section 2a is to be angularly bent in upward and downward directions, and four operating wires are threaded in upper, lower, right and left positions in the angle section 2b is to be bent in rightward and leftward directions as well as upward and downward directions. Fore ends of the operating wires 14 are fixedly anchored on a foremost angle ring of the angle section 2b or on the rigid tip end section 2c. Further, within the angle section 2b, the operating wires 21 are successively passed or threaded through the pivoting pins 14 or lancing arches which are formed in the angle rings 13. On the other hand, within the flexible body 2a, the operating wires 21 are passed through sheathing guide coils 22, which are each in the form of a tightly wound coil of a metallic wire with adjacent helices tightly closed to each other. The fore end of each closed sheathing coil 22 is securely fixed at a joint portion of the flexible body 2b with the angle section 2b, while the operating wires 21 are led out through the fixed end portion of the respective closed sheathing coils 22 and further extended forward through the angle section 2b.

Illustrated in FIG. 7 is the construction at and around the fixed fore ends of the closed sheathing coil 22 which serve as guide means for the operating wires 21. Anchor pins 23 are fixedly planted by caulking, for example, on the inner one of the two connecting rings 17 and 18, that is, on the connecting ring 18 on the side of the angle section 2b. Head portions 23a of the anchor pins 23 are located on the inner side of the connecting ring 18 and are each provided with a wire guide hole 24, in which an anchor pipe 25 is fixedly fitted by brazing or by other suitable means for fixing a fore end portion of a closed sheathing coil 22. The anchor pipe 25 is in the form of a stepped pipe having a large diameter portion 25a and a small diameter portion 25b. A fore end portion of each closed sheathing coil 22 is fixedly anchored in the large diameter portion 25a, for example, by brazing. An operating wire 21 alone is threaded through the smaller diameter portion 25b which is fitted in the guide hole 24 of the anchor pin 23, while the large diameter portion 25a is extended toward the flexible body 2a.

In assembling the insertion instrument 2, it is necessary to fix the two connecting rings 17 and 18 between the flexible body 2a and the angle section 2b firmly to each other. For this purpose, a flux is filled in the apertures 19 in the connecting ring 17 on the side of the flexible body 2a before applying solder to the apertures 19, thereby to distribute the solder all over the joining surfaces of the two connecting rings 17 and 18. By so doing, the connecting rings 17 and 18 can be fixed to each other securely over broader surface areas. Use of a large amount of flux may result in exudation of extra flux through gaps between the two connecting rings 17 and 18. Exudation of flux from end portions of the outer connecting ring 17 on the side of the flexible body 2a would not give rise to any serious problem in particular as long as it is relatively small in amount. However, flux which exudes from end portions of the inner connecting ring 18 on the side of the angle section 2b, if any, will get into internal portions of the insertion instrument 2, particularly into internal portions of the flexible body.

The operating wires 21 are passed internally of the end position of the connecting ring 18 on the side of the angle section 2b, along with the closed sheathing coils 22 in which the operating wires 21 are threaded. Each operating wire 21 is constituted by a large number of stranded fine metal filaments, and slid within the closed sheathing coil 22 at the time of flexibly bending the angle section 2b. The above-mentioned flux, which has migrated into internal portions of the insertion instrument 2 from end portions of the connecting ring 18 on the side of the angle section 2b, can get into the closed sheathing coils 22 and stick on the surface of the operating wires 21 to cause oxidation of the constituent fine metal wires of the operating wires 21. Under such circumstances, due to corrosive deteriorations, the operating wires 21 are subjected to abrasive wear in a conspicuously increased degree while in sliding contact with the closed sheathing coils 22 and are caused to break in a worst case.

SUMMARY OF THE INVENTION

With the foregoing situations in view, it is an object of the present invention to provide a joint construction for connecting an angle section to an elongated flexible body of an endoscopic insertion instrument, which permits to solder the angle section and the flexible body firmly and securely together by the use of a flux in such a way as to preclude possibilities of flux deposition on operating wires of the angle section.

It is another object of the present invention to provide a joint construction for connecting an angle section to an elongated flexible body of an endoscopic insertion instrument, which can ensure smooth movements of angle section operating wires within closed sheathing coils even if a relatively large amount of flux is applied to increase soldering surface areas of connecting rings.

It is still another object of the present invention to provide a joint construction for connecting an angle section to an elongated flexible body of an endoscopic insertion instrument, which can improve durability of angle section operating wires.

In order to achieve the above-stated objectives, according to the present invention, there is provided a joint construction for an endoscopic insertion instrument which is basically composed of a rigid tip end section with an observation window and an illumination window, an elongated flexible body, and an angle section connected between said rigid tip end section and said flexible body. More particularly, according to the present invention, there is provided a joint construction for connecting an angle section to a fore end of a flexible body of an endoscopic insertion instrument, which comprises: a couple of connecting rings opposingly provided at joining ends of the angle section and the flexible body for fitting engagement with each other, one on the outer side of the other one; an aperture or a plural number of apertures provided in an outer one of the connecting rings to supply solder to overlapped joining surfaces of the connecting rings at the time of fixedly soldering the connecting rings to each other; at least one operating wire threaded and extended through the angle section and the elongated flexible body of the insertion instrument via the connecting rings for flexibly bending the angle section; a closed sheathing coil coextensively provided in the flexible body for encasing the operating wire and having a fore end portion thereof securely fixed to an inner one of the connecting rings; and a fluid-tight shield portion formed on and around outer periphery of the closed sheathing coil over a predetermined range in axial length, including at least proximal end portions of the inner connecting ring, to prevent a flux from intruding into the closed sheathing coil at the time of soldering the connecting rings together.

In this instance, the closed sheathing coil can be fixed to one of the connecting rings either directly or through an anchor pipe. For example, the anchor pipe can be constituted by a large diameter portion which is to receive a fore end portion of the closed sheathing coil, and a small diameter portion which is fixedly stopped in an inner one of the connecting rings by an anchor pin and internally provided with an axial wire passage for threading therethrough an operating wire coming out of the closed sheathing coil. In a case where the anchor pipe is arranged in the way just described, the shield portion is formed to cover the outer periphery of the closed sheathing coil over a predetermined range in axial length from the large diameter portion of the anchor pipe. In this case, it is the connecting ring on the side of the angle section to which the closed sheathing coil is connected either directly or through an anchor pipe.

In a case where the closed sheathing coil is fixed by the use of an anchor pipe, the shield portion is formed on and around the closed sheathing coil in such a way that it is connected to the anchor pipe at one end and extended into the flexible body of the insertion instrument at the other end thereof. Preferably, the other end of the shield portion is axially extended beyond the connecting ring on the side of the flexible body and into a helical coil structure which forms a bone structure of the flexible body. Further, preferably the shield portion is constituted by a soft and resilient structure although this is not a mandatory requisite. In one preferred form of the invention, the shield portion is formed by applying a soft and resilient seal material on and around the outer periphery of a closed sheathing coil portion on the proximal side of the anchor pipe. Alternatively, the shield portion can be formed by fitting a flexible tube on the outer periphery of the closed sheathing tube.

The above and other objects, features and advantages of the present invention will become apparent from the following particular description of the invention, taken in conjunction with the accompanying drawings which show by way of example some preferred embodiments of the invention. Needless to say, the present invention should not be construed as being limited to particular exemplary forms shown.

DESCRIPTION OF PREFERRED EMBODIMENTS

Figure 1:
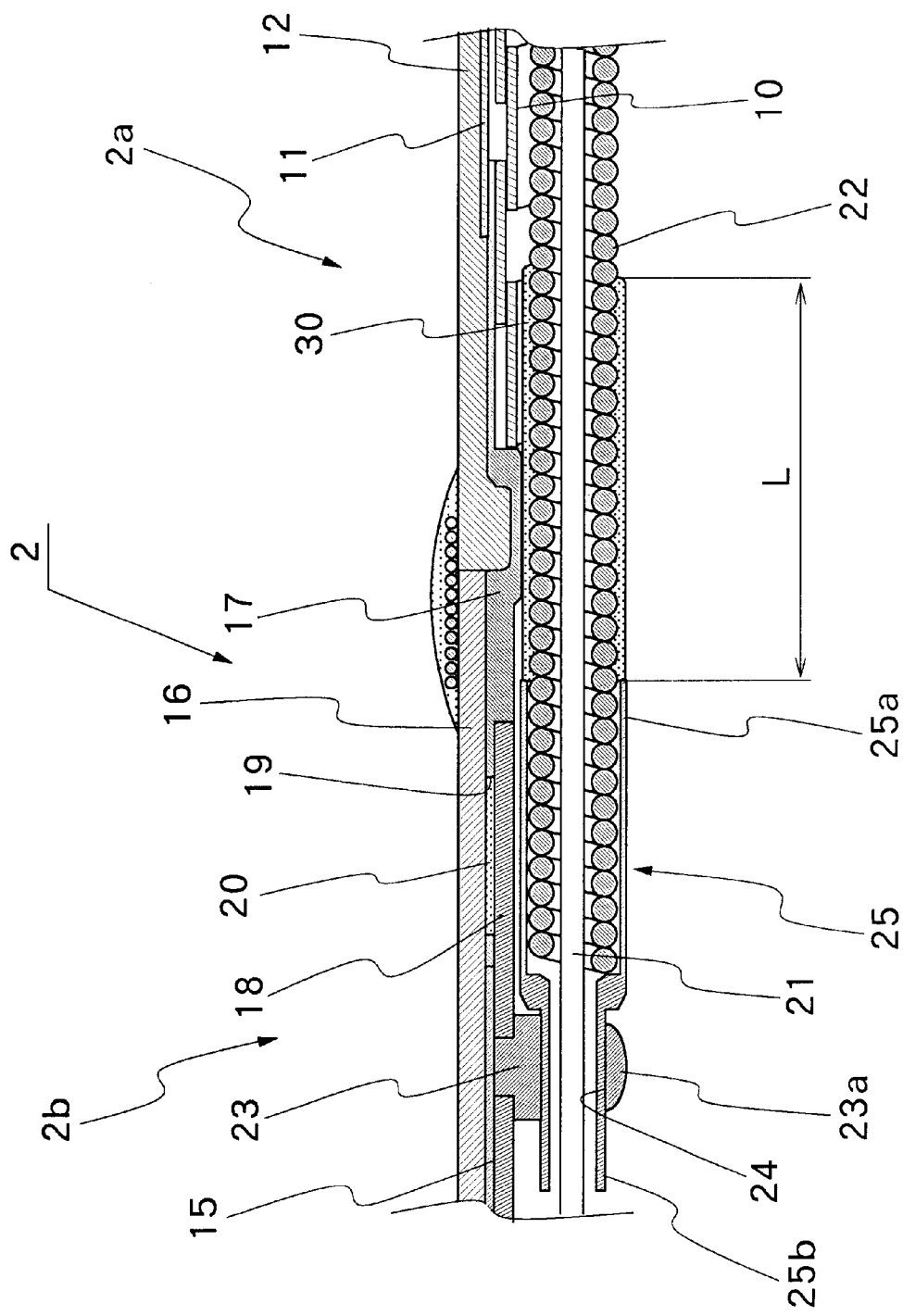
FIG. 1 is a schematic sectional view of an operating wire guide which is adopted in a first embodiment of the present invention.

Hereafter, the present invention is described more particularly by way of its preferred embodiments with reference to the accompanying drawings. In the following description of preferred embodiments, those component parts which are equivalent or identical with the counterparts in the above-discussed prior art are designated by similar reference numerals or characters to avoid repetitions of same explanations.

Figure 2:
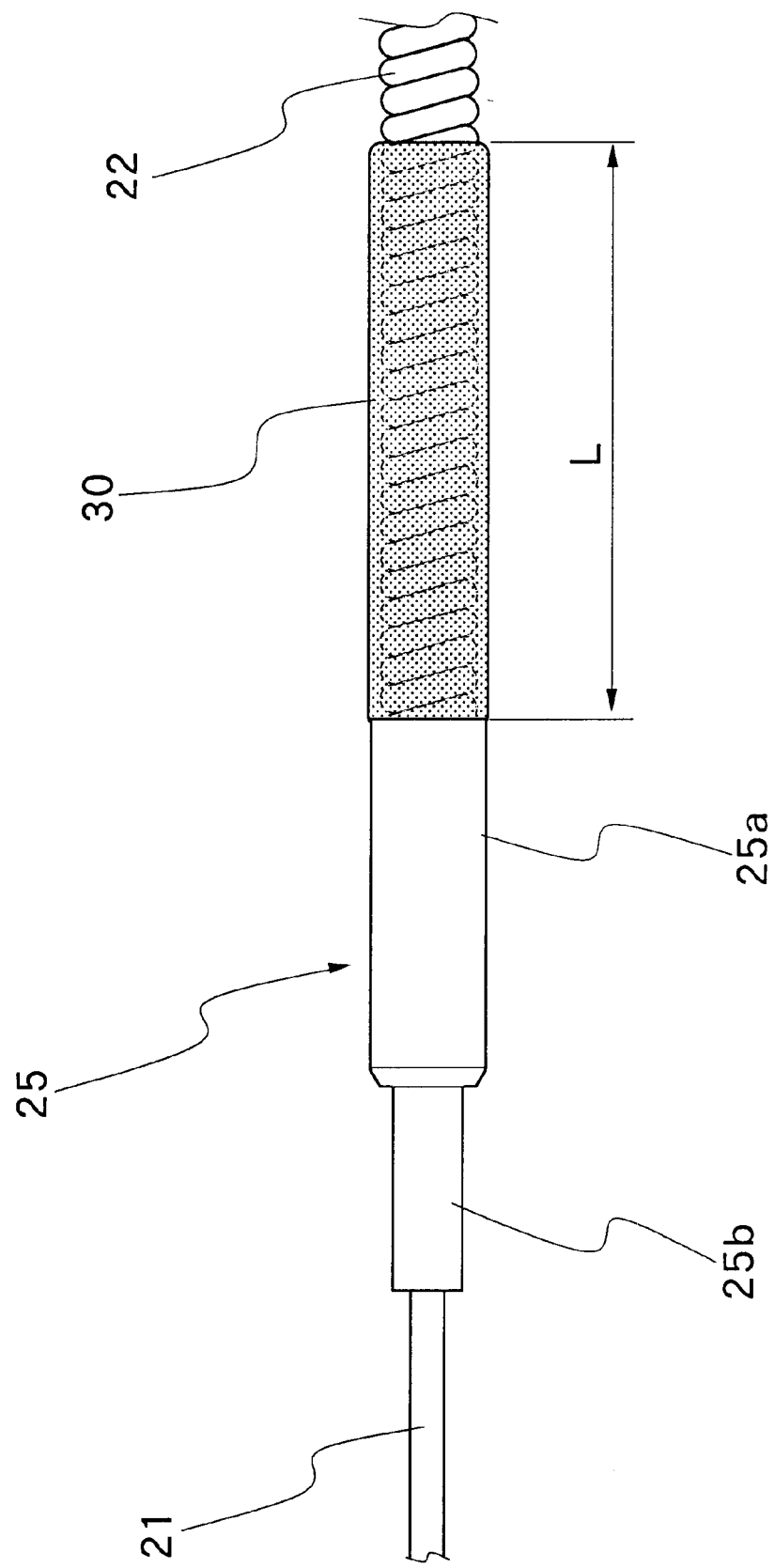
FIG. 2 is an outer view of an operating wire which is threaded in an anchor pipe.

Referring to FIGS. 1 and 2, there is shown a first embodiment of the present invention. In these figures, indicated at 25 is an anchor pipe which is fixed to a connecting ring 18 on the side of an angle section 2a of an endoscopic insertion instrument 2 by means of an anchor pin 23. Similarly to the counterpart in the above-described prior art, the anchor pipe 25 is constituted by a large diameter portion 25a and a small diameter portion 25b, and a fore end portion of a tightly closed sheathing coil 22 of an operating wire 21 is fixedly fitted in the large diameter portion 25a. More specifically, as shown in FIG. 2, the fore end of the tightly closed sheathing coil 22 which is fitted in the large diameter portion 25a in the shape of a circular tube is abutted against a stepped portion between the large and small diameter portions 25a and 25b and securely fixed to the anchor pipe 25 by conducting laser spot welding from the side of circumferential surface of the large diameter portion 25a. The tightly closed sheathing coil 22 may be welded to the anchor pipe 25 only at one spot because, once assembled into an endoscopic insertion instrument, they will not be subject to large external forces. However, the number of welding spots may be increased for the purpose of stabilizing the connection of these parts.

A seal material 30 is applied to form a shield portion on and around the circumference of the closed sheathing guide coil 22 on the posterior side of the anchor pipe 25, over a predetermined axial length L across a proximal end of the anchor pipe 25. In this instance, the seal material 30 is of a soft and resilient type which can fill in and hermetically seal the gaps between the helices of the closed sheathing coil 22 which is in the range of the above-mentioned axial length L. The closed sheathing coil 22, however, is flexible in bending directions. Namely, the closed sheathing coil 22 is formed into the shape of a tunnel which is circumferentially closed by the seal material 30 and which is extended across the proximal end of the anchor pipe 25 over the axial length L.

Thus, the closed sheathing guide coil 22 is partially hermetically closed by the seal material 30 as described above, for the purpose of preventing a flux from getting into the coil 22 at the time of joining and soldering the connecting rings 17 and 18 to each other. At this time, a flux is used for the purpose of letting solder sufficiently get on and spread over broad joining surface areas of the connecting rings 17 and 18 which are fitted one on the other substantially in a tightly closed state. Accordingly, the coil portion which is hermetically encased in the seal material 30 functions to block intrusion of the flux. In order to produce the flux blocking function to a sufficient degree, the seal material 30 should be applied over the axial length L which extends at least as far as a position on the proximal side of the inner connecting ring 17 on the part of the angle section 2b, more specifically, a position inward of the coil tube 10 as shown in FIG. 1.

With the arrangements just described, at the time of joining the angle section 2b with the flexible body 2a of the insertion instrument 2 by soldering, a sufficient amount of flux can be filled into the apertures 19 in the connecting ring 17 on the side of the angle section 2b. As solder is put into the apertures 19, the flux is pushed apart and an excess amount of flux is caused to exude from a gap space between the two connecting rings 17 and 18 in a direction radially inward of the flexible body 2a. However, at this position, the closed sheathing coil 22 is hermetically enshrouded in the seal material 30, so that there is no possibility of the flux depositing on the operating wire 21 which is threaded in the closed sheathing coil 22. Accordingly, the joint construction according to the invention contributes to protect operating wire 21 against oxidative deteriorations by the flux and to prolong the service life of the operating wire 21 by suppressing the abrasive wear which results from sliding contact with the closed sheathing coil 22. In addition, the joint construction contributes to ensure smooth sliding movements of the operating wire 21 within the closed sheathing coil 22. Further, the use of a sufficient amount of flux in joining and fixing the flexible body portion 2a and angle section 2b with each other makes it possible to distribute solder over broad joining surface areas of the connecting rings 17 and 18 and thus to improve the strength of connection between the two connecting rings.

From the standpoint of preventing intrusion of a flux, it is desirable to increase as much as possible the axial length of coil portion which is circumferentially sealed with the seal material 30. However, resistance to bending movements is increased to a certain degree in case the seal material 30 is applied in such a way to fill in interstices between individual helices of the closed sheathing coil 22 even if the seal material 30 is of a soft and resilient type. In this connection, considering that applied flux tends to exude and flow into the insertion instrument from end portions of the connecting ring 18 on the side of the angle section 2b, the range of application of the seal material 30 should be extended at least to a position further on the proximal side of the proximal end of the connecting ring 18.

At the joint of the flexible body 2a and the angle section 2b of the insertion instrument, the connecting ring 18 on the side of the angle section 2b and the connecting 17 on the side of the flexible body 2a are located in an unbendable rigid portion in the path of the operating wire 21. The fore end of the closed sheathing coil 22 is connected to the anchor pipe 25 which is located in the unbendable rigid portion. In this regard, it is important to locate the anchor pipe 25 within the range of the unbendable rigid portion. The flexible body 2a is less bendable in a transitional portion which extends over a certain length from the unbendable rigid portion. Accordingly, a drop in bending flexibility by application of the seal material 30 around the circumference of the closed sheathing coil 22 will not give rise to a problem in particular as long as it is located in the above-mentioned transitional portion of the flexible body 2a. Accordingly, a shield portion which is formed on and around the closed sheathing coil 22 by application of the seal material 30 can be extended as far as the less bendable transitional portion. More specifically, the seal material 30 is applied such that the shield portion is preferably extended as far as a position slightly inward of the coil tube 10 in the flexible body 2a. By so arranging the shield portion, it becomes possible to prevent intrusion of a flux more securely without impairing necessary bending flexibility of the closed sheathing coil 22.

Figure 3:
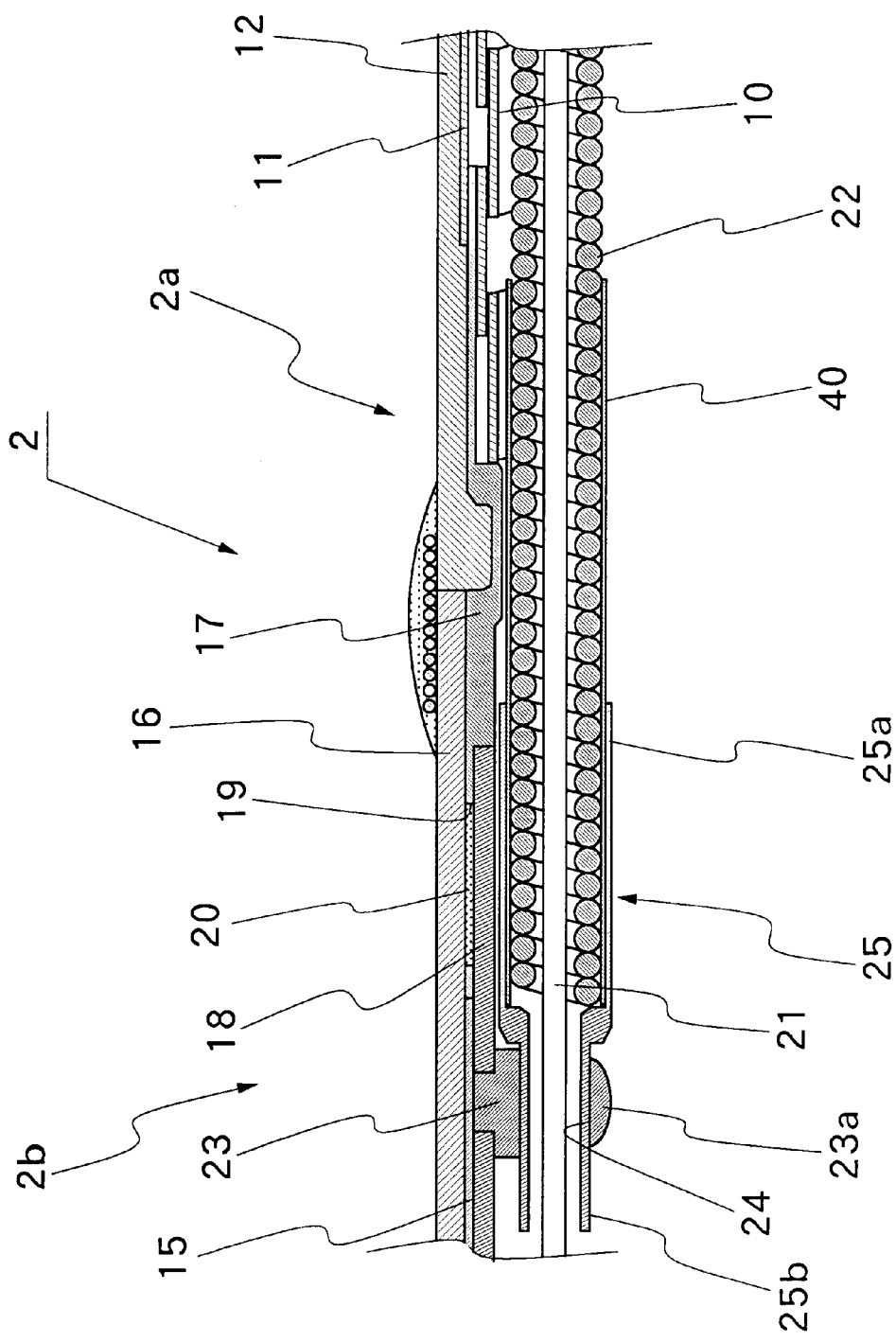
FIG. 3 is a schematic sectional view of an operating wire guide which is adopted in a second embodiment of the invention.

Turning now to FIG. 3, there is shown a second embodiment of the present invention, in which a shield is formed by fitting a flexible shield tube 40 on the circumference of the closed sheathing coil 22 instead of applying a seal material thereon. Similarly to the shield portion in the foregoing first embodiment, the flexible tube 40 has a length which extends from a position in the anchor pipe 25 to a position in the less bendable transitional portion of the flexible body 2a. In this instance, for example, the flexible tube 40 is formed of a thermally contractible material and tightly fitted on the closed sheathing coil 22 by application of heat after it is set in position on the anchor pipe 25 and the sheathing coil 22. Upon fitting the flexible shielding tube 40 on the closed sheathing coil 22 in this manner, the interstices between the individual helices of the coil 22 are completely closed by the tube 40 to block a flux which might otherwise intrude into the closed sheathing coil 22 and deposit on the operating wire 21 when soldering the connecting rings 17 and 18 for joining the angle section 2b to the flexible body 2a of the insertion instrument 2.

Figure 4:
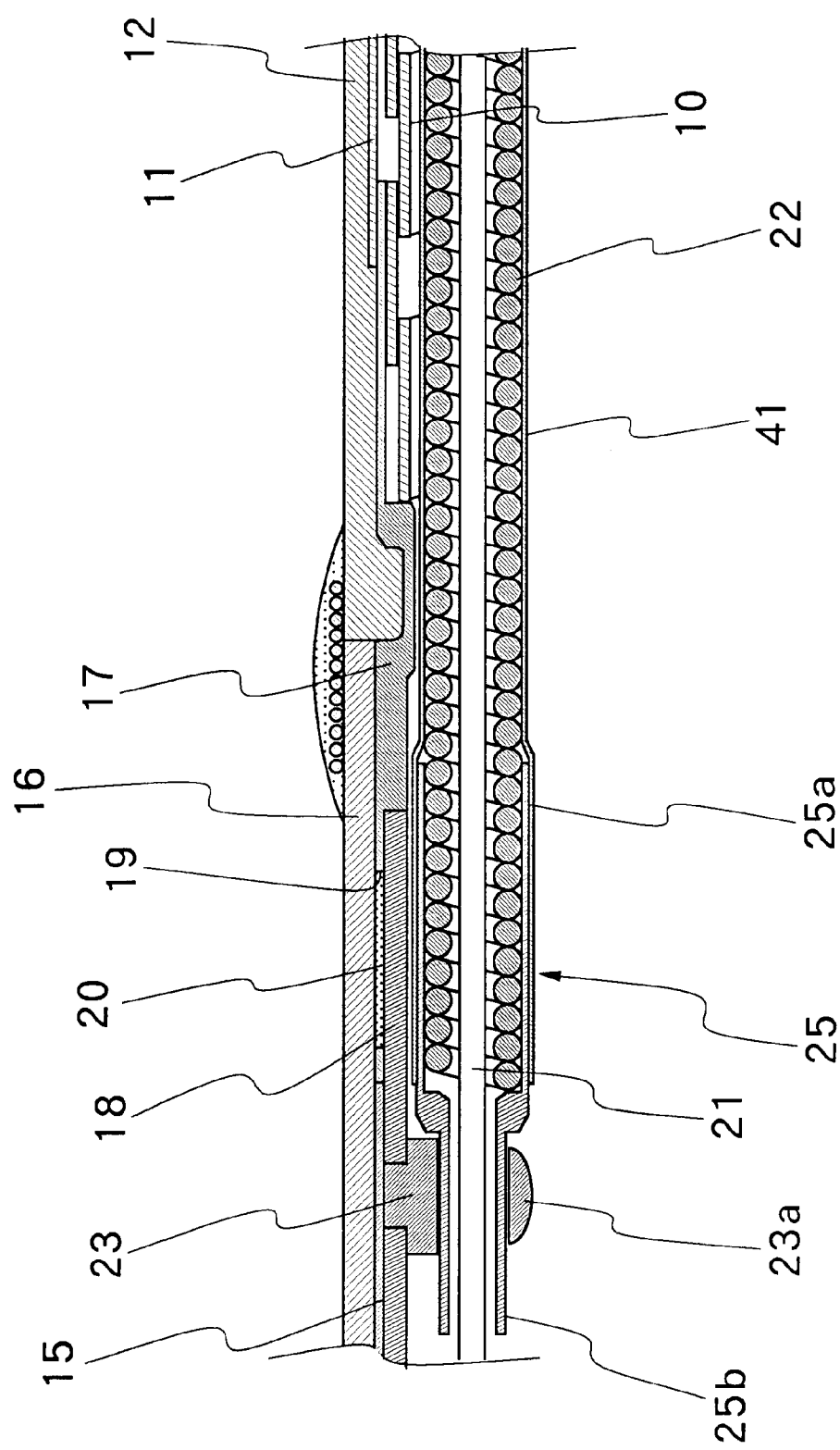
FIG. 4 is a schematic sectional view of an operating wire guide which is adopted in a third embodiment of the invention.
Figure 5:
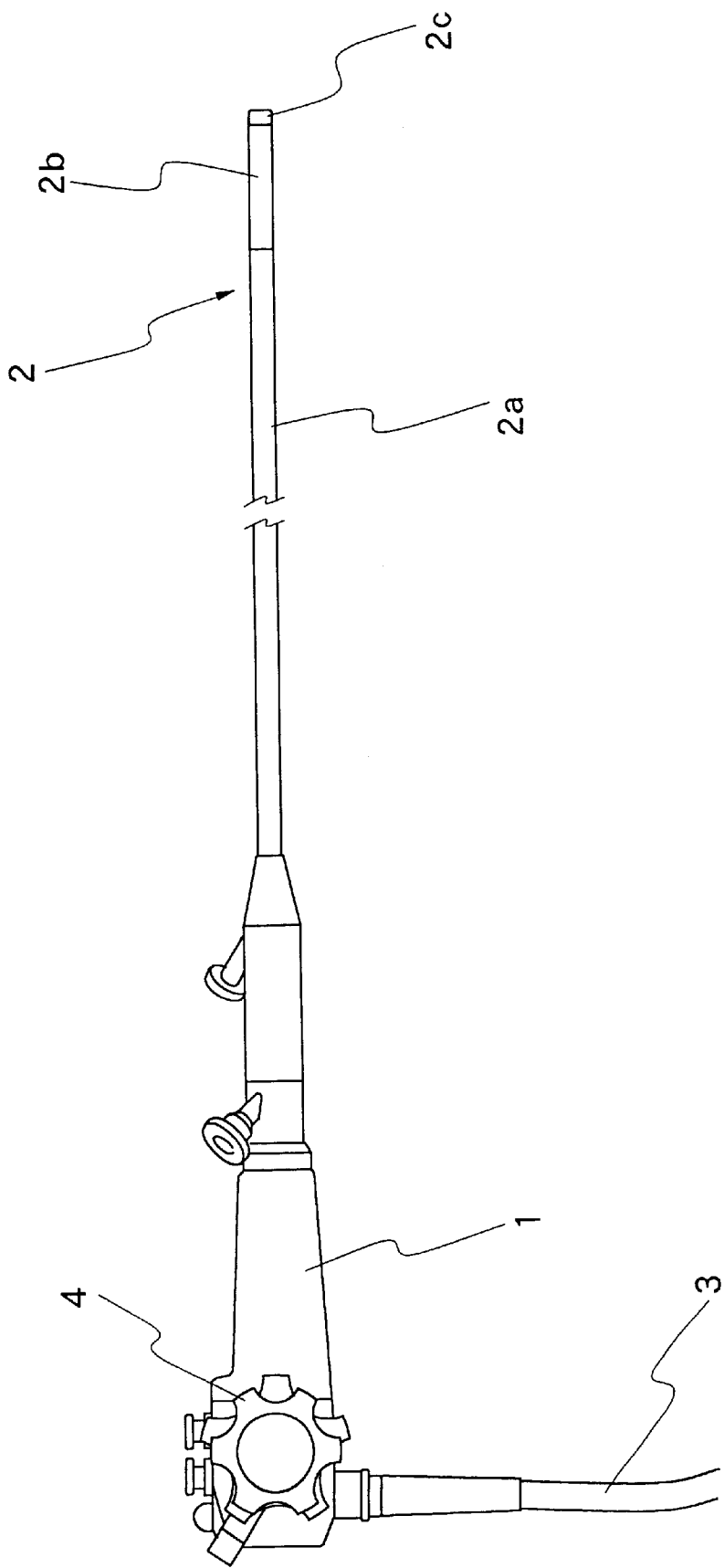
FIG. 5 is an outer view of an endoscope having an insertion instrument which is generally known in basic construction.
Figure 6:
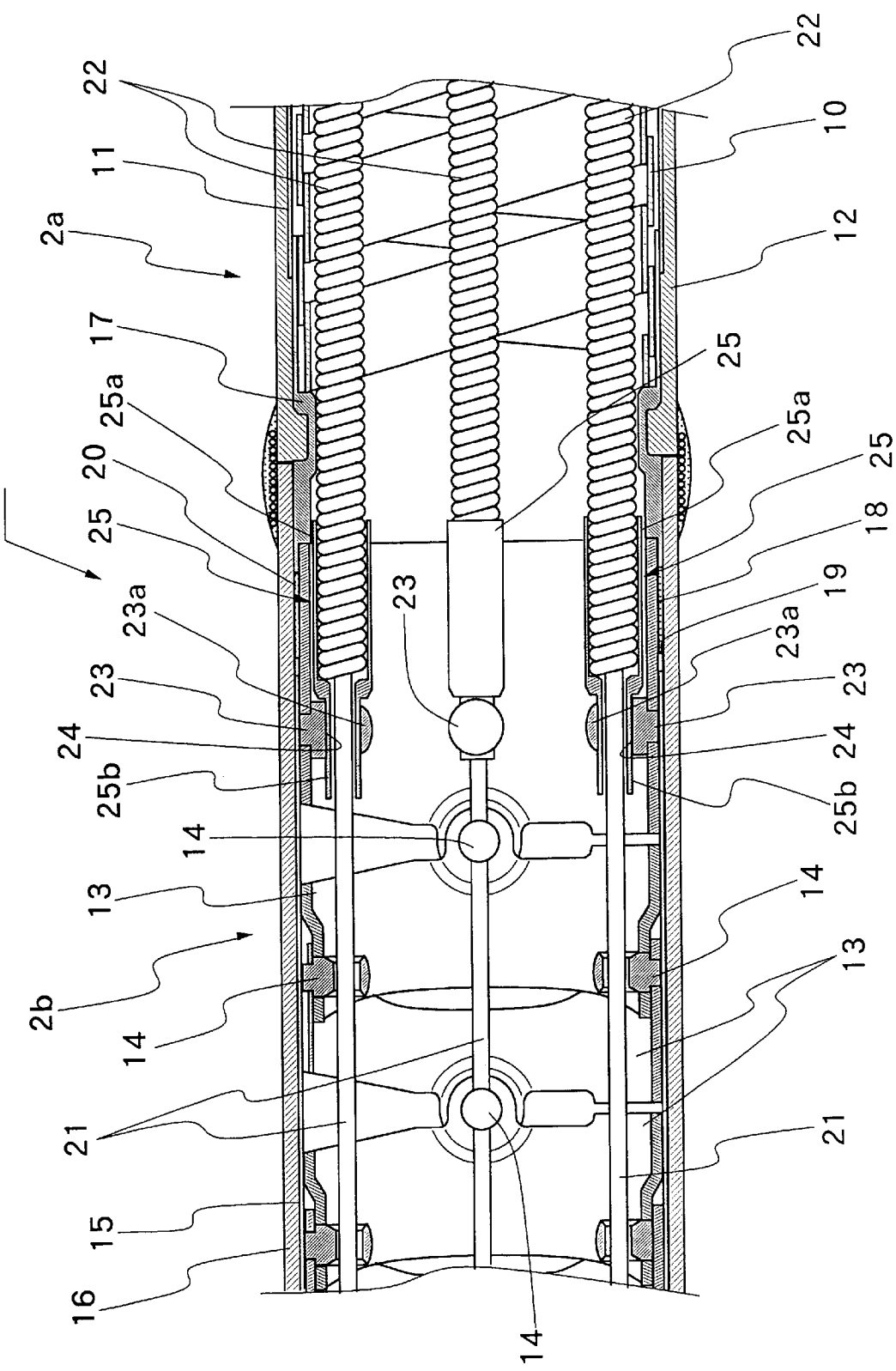
FIG. 6 is a schematic sectional view taken through a joint portion of an angle section and an elongated flexible body of the known endoscopic insertion instrument.
Figure 7:
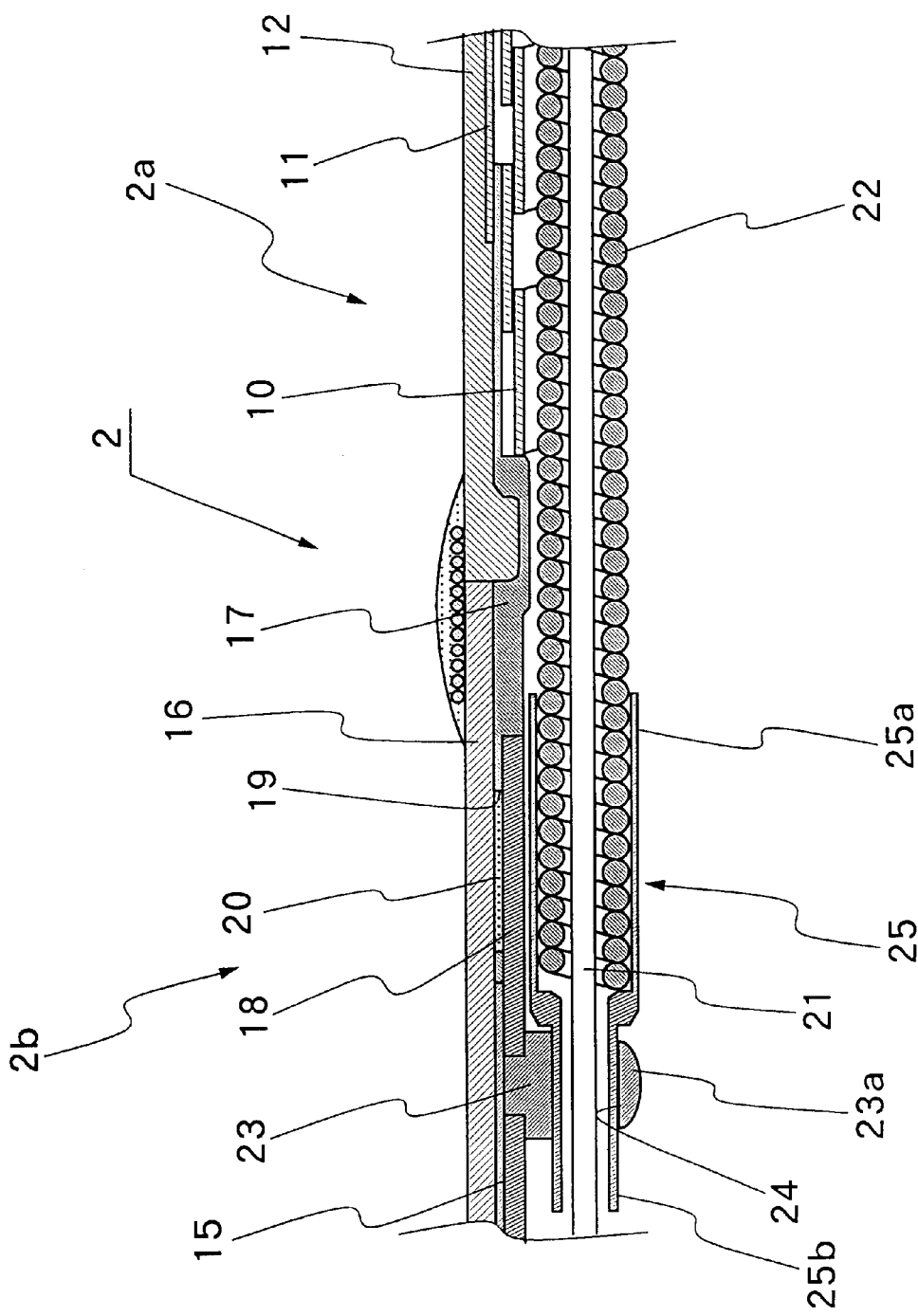
FIG. 7 is an enlarged sectional view of the joint portion shown in FIG. 6.

In the case of the embodiment shown in FIG. 3, the flexible shield tube 40 is fitted on the closed sheathing tube 22 before inserting and fixing same to the anchor pipe 25. However, as shown in FIG. 4, a flexible shield tube 41 may be fitted on the closed sheathing coil 22 and the large diameter portion 25a after inserting the closed sheathing coil 22 into the anchor pipe and securely fixing these parts together by laser spot welding or by other suitable fixation means. In this case, it is important for the flexible shield tube 41, which is fitted on the closed sheathing coil 22, to be arranged to cover at least proximal end portions of the large diameter portion 25a of the anchor pipe 25.

What is claimed is:

1. In an endoscopic insertion instrument having a rigid tip end section with an observation window and an illumination window, an elongated flexible body, and an angle section connected between said rigid tip end section and said flexible body:

a join construction configured to connect said angle section to said flexible body of said endoscopic insertion instrument, comprising:

a couple of connecting rings axially extended toward each other from joining ends of said angle section and said flexible body and fitted one on the other one in an overlapped state;

at least one aperture provided in an outer one of said connecting rings to supply solder to overlapped joining surfaces of said connecting rings at the time fixedly soldering said connecting rings to each other;

at least one operating wire threaded and extended through said angle section and said elongated flexible body of said insertion instrument via said connecting rings configured to flexibly bend said angle section;

a closed sheathing coil coextensively provided in said flexible body configured to encase said operating wire;

an anchor pipe fixedly provided in the inner one of said connecting rings to fixedly anchor a fore end of said sheathing coil; and a fluid-tight shield portion formed on and around outer periphery of said closed sheathing coil over a predetermined axial length at least from a proximal end portion of said inner connecting ring, to prevent a flux from intruding into said closed sheathing coil at the time of soldering said connecting rings together.

2. A joint construction for an endoscopic insertion instrument as defined in claim 1, wherein said anchor pipe is in the shape of a stepped pipe having a small diameter portion on the front side of a large diameter portion and is adapted to anchor a fore end portion of said closed sheathing coil in said large diameter portion, said small diameter portion internally proving a passage for said operating wire toward said angle section and said shield portion being formed over a predetermined axial length from a proximal end of said large diameter portion toward said flexible body of said insertion instrument.

3. A joint construction for an endoscopic insertion instrument as defined in claim 2, wherein said anchor pipe is fixedly stopped in said inner connecting ring by means of an anchor pin.

4. A joint construction for an endoscopic insertion instrument as defined in claim 1, wherein said inner connecting ring is a connecting ring on the side of said angle section of said insertion instrument.

5. A joint construction for an endoscopic insertion instrument as defined in claim 4, wherein said shield portion is of a flexible structure and extended into a helical coil structure of said flexible body of said insertion instrument beyond said connecting ring on the side of said flexible body.

6. A joint construction for an endoscopic insertion instrument as defined in claim 5, wherein said shield portion is formed by applying a resilient seal material on and around an outer periphery of said closed sheathing coil over a predetermined axial length from a proximal end of said anchor pipe toward said flexible body of said insertion instrument.

7. A joint construction for an endoscopic insertion instrument as defined in claim 5, wherein said shield portion is formed by fitting a flexible tube on outer periphery of said closed sheathing coil.

8. In an endoscopic insertion instrument having a rigid tip end section with an observation window and an illumination window, an elongated flexible body, an angle section connected between said rigid tip end section and said flexible body, inner and outer connecting ring extended toward each other from meeting ends of said angle section and said flexible body and fitted one on the other in an overlapped state, said inner and outer rings being soldered together to join said angle section and said flexible body fixedly to each other:

an endoscopic insertion instrument comprising:

an operating wire passed through a joint portion of said connecting rings to turn said angle section into an angularly bent position;

a sheathing coil coextensively provided in said flexible body and configured to encase said operating wire;

an anchor pipe fixedly provided at the joint portion of said connecting rings and configured to anchor a fore end portion of said sheathing coil therein; and a fluid-tight shield portion provided around said sheathing coil over a predetermined axial length from a proximal end of said anchor pipe and extended into a helical coil structure of said flexible body to prevent intrusion of solder into said sheathing coil at the time of soldering said connecting rings together.

9. An endoscopic insertion instrument as defined in claim 8 wherein said shield portion is constituted by a seal material which is applied on outer periphery of said sheathing coil.

10. An endoscopic insertion instrument as defined in claim 8, wherein said shield portion is constituted by a flexible tube which is fitted on outer periphery of said sheathing tube.

* * * * *